United States Patent
Williamson et al.

(10) Patent No.: US 10,383,960 B2
(45) Date of Patent: Aug. 20, 2019

(54) SMALL MOLECULE IMAGING OF FUNGI BY POSITRON EMISSION TOMOGRAPHY SCANNING

(71) Applicants: The United States of America, as represented by the Secretary, Department of Health and Human Services, Washington, DC (US); The Reearch Foundation of the State University of New York, Amherst, NY (US)

(72) Inventors: Peter R. Williamson, Bethesda, MD (US); Dale O. Kiesewetter, Gaithersburg, MD (US); John Panepinto, Buffalo, NY (US); Jin Qiu, Bethesda, MD (US)

(73) Assignees: The United States of America, as Represented by the Secretary, Department of Health and Human Services, Washington, DC (US); The Research Foundation of the State Univeristy of New York, Amherst, NY (US)

( * ) Notice: Subject to any disclaimer, the term of this patent is extended or adjusted under 35 U.S.C. 154(b) by 0 days.

(21) Appl. No.: 15/961,554

(22) Filed: Apr. 24, 2018

(65) Prior Publication Data
US 2018/0236111 A1    Aug. 23, 2018

Related U.S. Application Data

(62) Division of application No. 15/030,554, filed as application No. PCT/US2014/061917 on Oct. 23, 2014, now Pat. No. 9,968,693.
(Continued)

(51) Int. Cl.
C07D 251/68    (2006.01)
A61K 31/53    (2006.01)
(Continued)

(52) U.S. Cl.
CPC .......... A61K 51/0461 (2013.01); A61K 31/53 (2013.01); C07B 59/002 (2013.01); C07D 251/68 (2013.01)

(58) Field of Classification Search
CPC ...... C07D 251/70; A61K 31/53; A61K 51/04; C07B 59/002
(Continued)

(56) References Cited

U.S. PATENT DOCUMENTS 3,951,965 A    4/1976 Mengler et al.
9,968,693 B2*    5/2018 Williamson ......... C07D 251/68
2012/0134920 A1    5/2012 D'Souza et al.

FOREIGN PATENT DOCUMENTS

CN    101298438    11/2008

OTHER PUBLICATIONS

Fowler, et al. "PET and drug research and development." *The Journal of Nuclear Medicine* 40, No. 7 (1999): 1154.
(Continued)

*Primary Examiner* — Venkataraman Balasubramanian
(74) *Attorney, Agent, or Firm* — Klarquist Sparkman, LLP

(57) ABSTRACT

Disclosed herein are isotopically labeled calcofluor derivatives and uses of such to detect fungi, such as filamentous fungi, including *Aspergillus* species, such as by positron emission tomography (PET) scanning. In some examples, the disclosed compounds have a formula of

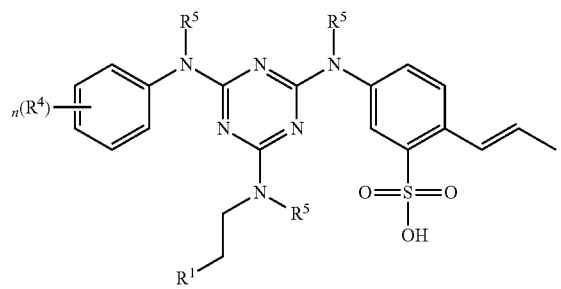

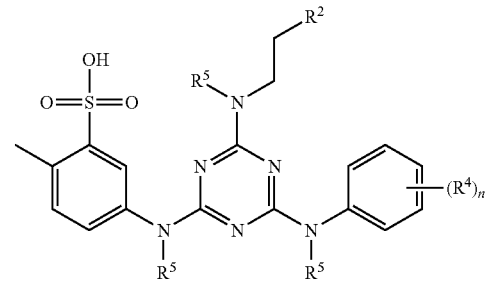

wherein $R^1$ is an amine, a hydroxyl group, a sulfide, a carboxylic acid, an amide, an alkyl, or aryl; $R^2$ is —NHC(O)—$R^3$-L or —C(O)NH—$R^3$-L, wherein $R^3$ is an aryl or an aliphatic group (such as alkyl); each $R^4$ independently may be selected from halogen, aliphatic (such as alkyl), aryl, amine, hydroxyl, haloalkyl, carboxylic acid, amide, aralkyl, cyano, ester, thiol, thioether, or alkoxy; each $R^5$ independently may be selected from hydrogen, aralkyl, alkyl, or aryl, with any one of the aralkyl, alkyl, or aryl groups optionally being substituted with any one of the substituents provided for $R^4$; each n independently is 1, 2, 3, 4, or 5; and L is $^{18}$F or a chelator capable of chelating a radiolabel (such as chelators for [$^{18}$F]AlF, $^{64}$Cu, $^{68}$Ga), 1,4,7,10-tetraazacyclododecane-tetraacetic acid (DOTA) or 1,4,7-triazacyclononane-triacetic acid (NOTA).

19 Claims, 2 Drawing Sheets

Related U.S. Application Data

(60) Provisional application No. 61/894,754, filed on Oct. 23, 2013.

(51) Int. Cl.
*A61K 51/04* (2006.01)
*C07B 59/00* (2006.01)

(58) Field of Classification Search
USPC ............... 544/193.2; 514/245; 540/474; 424/9.363
See application file for complete search history.

(56) References Cited

OTHER PUBLICATIONS

International Search Report and Written Opinion for PCT/US2014/061917, dated Dec. 4, 2014, by the European Patent Office as International Searching Authority (10 pages).

Kim, et al. "Chemosensitization prevents tolerance of Aspergillus futnigatus to antimycotic drugs." *Biochemical and Biophysical Research Communications* 372, No. 1 (2008): 266-271.

Lackner, et al. "Species-specific antifungal susceptibility patterns of *Scedosporiuni* and *Pseudallescheria* species." *Antimicrobial Agents and Chemotherapy* 56, No. 5 (2012): 2635-2642.

Petrik, et al. "68Ga-siderophores for PET imaging of invasive pulmonary aspergillosis: proof of principle," *Journal of Nuclear Medicine* 51, No. 4 (2010): 639-645.

Ram, et al. "Identification of fungal cell wall mutants using susceptibility assays based on Calcofluor white and Congo red," *Nature Protocols* 1, No. 5 (2006): 2253-2256.

Wahl, et al. "Regions of interest in the venous sinuses as input functions for quantitative PET." *The Journal of Nuclear Medicine* 40, No. 10 (1999): 1666.

Yao, et al. "Quantitative PET Imaging of Bone Marrow Glucose Metabolic Response to Hematopoietic Cytokines." *The Journal of Nuclear Medicine* 36 (1995): 794-799.

\* cited by examiner

US 10,383,960 B2

SMALL MOLECULE IMAGING OF FUNGI BY POSITRON EMISSION TOMOGRAPHY SCANNING

CROSS REFERENCE TO RELATED APPLICATIONS

This is a divisional of U.S. application Ser. No. 15/030,554, filed Apr. 19, 2016, issued as U.S. Pat. No. 9,968,693 on May 15, 2018, which is the U.S. National Stage of International Application No. PCT/US2014/061917, filed Oct. 23, 2014, which was published in English under PCT Article 21(2), which in turn claims the benefit of U.S. Provisional Patent Application No. 61/894,754, filed on Oct. 23, 2013. Each of the prior applications is incorporated by reference herein in its entirety.

FIELD

This relates to the field of radioactive, isotopically-labeled calcofluor derivatives and uses of such to detect fungi, such as filamentous fungi including *Aspergillus* species, such as by positron emission tomography (PET) scanning.

BACKGROUND

*Aspergillus* is a common fungus that is typically not a pathogen, but in immunosuppressed patients, such as those undergoing chemotherapy or stem cell/solid organ transplant, it can be a highly lethal disease with approximately 50% mortality, even with therapy. The disease is often first detected by a nodule in the lung on a computed tomography (CT) scan. Typically, a bronchoscope is placed into the lung and fluid is aspirated, which can make a diagnosis. Alternatively, a lung biopsy can be performed, by inserting a small needle into the lung and withdrawing lung tissue. Both procedures have significant morbidity/mortality and their yield is suboptimal. Noninvasive imaging can detect a nodule, but the nodule may be due to cancer, or other bacterial infections or unusual infections such as *nocardia*. Thus, a need exists for a noninvasive diagnostic test specific for fungal infections.

SUMMARY

Disclosed herein are radioactive, isotopically-labeled calcofluor derivatives, including a compound according to the formula

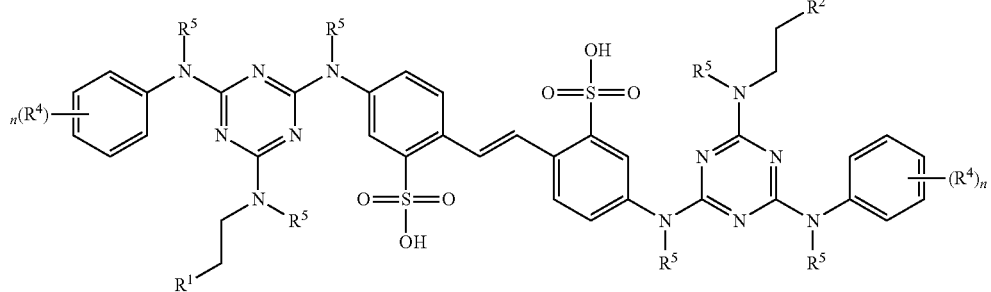

wherein $R^1$ is an amine, a hydroxyl group, a sulfide, a carboxylic acid, an amide, an alkyl, or aryl; $R^2$ is —NHC(O)—$R^3$-L or —C(O)NH—$R^3$-L, wherein $R^3$ is an aryl or an aliphatic group (such as alkyl); each $R^4$ independently may be selected from halogen, aliphatic (such as alkyl), aryl, amine, hydroxyl, haloalkyl, carboxylic acid, amide, aralkyl, cyano, ester, thiol, thioether, or alkoxy; each $R^5$ independently may be selected from hydrogen, aralkyl, alkyl, or aryl, with any one of the aralkyl, alkyl, or aryl groups optionally being substituted with any one of the substituents provided for $R^4$; each n independently is 1, 2, 3, 4, or 5; and L is $^{18}F$ or a chelator capable of chelating a radiolabel (such as chelators for [$^{18}F$]AlF, $^{64}Cu$, $^{68}Ga$), 1,4,7,10-tetraazacyclododecane-tetraacetic acid (DOTA) or 1,4,7-triazacyclononane-triacetic acid (NOTA). In some particular embodiments, L is $^{18}F$.

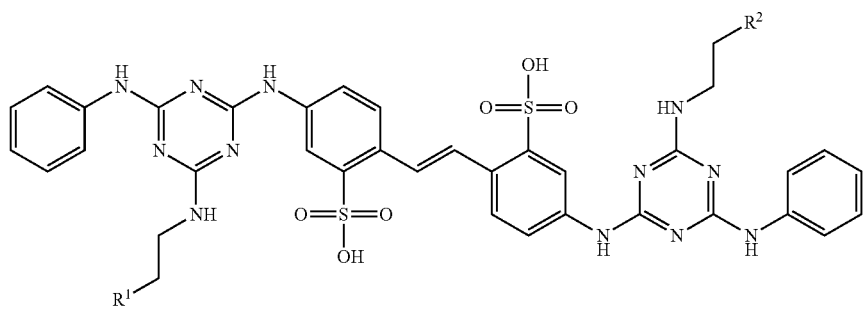

wherein $R^1$, $R^2$, and L are as provided above. In particular disclosed embodiments, $R^2$ is —NHC(O)—$R^3$-L or —C(O)NH—$R^3$-L, wherein $R^3$ is an aryl group comprising an L group in any position on the ring. For example, L may be located in the ortho position, the mew position, the para position, or combinations thereof. In some embodiments wherein $R^3$ is an aryl group, the aryl group may comprise one or more additional substituents, selected from halogen, aliphatic (such as alkyl), aryl, amine, hydroxyl, haloalkyl, carboxylic acid, amide, aralkyl, cyano, ester, thiol, thioether, or alkoxy.

In some embodiments, a compound has the formula

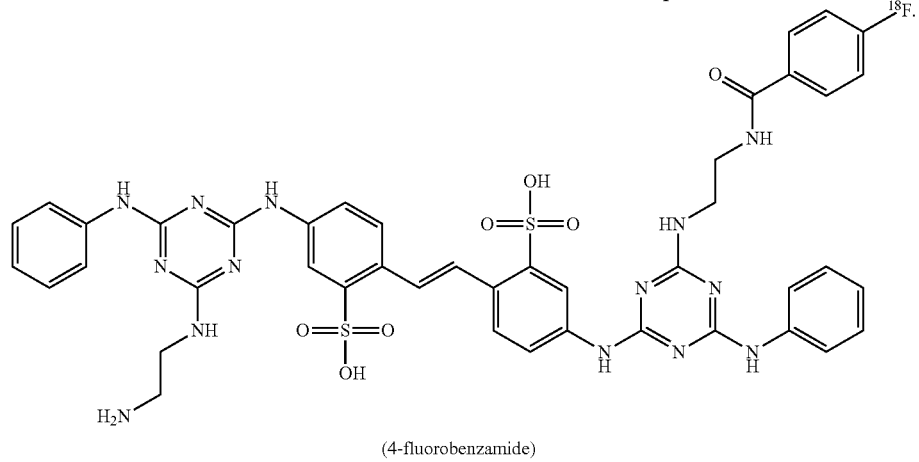

(4-fluorobenzamide)

In some embodiments, a compound has the formula

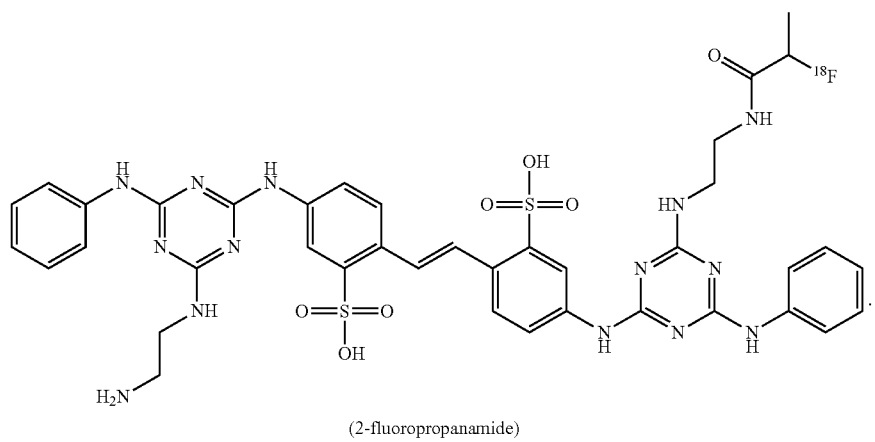 [SMILES: CC([18F])C(=O)NCCNc1nc(Nc2ccccc2)nc(Nc2ccc(/C=C/c3ccc(Nc4nc(NCCN)nc(Nc5ccccc5)n4)cc3S(=O)(=O)O)c(S(=O)(=O)O)c2)n1]

(2-fluoropropanamide)

In some embodiments, the compound has the formula

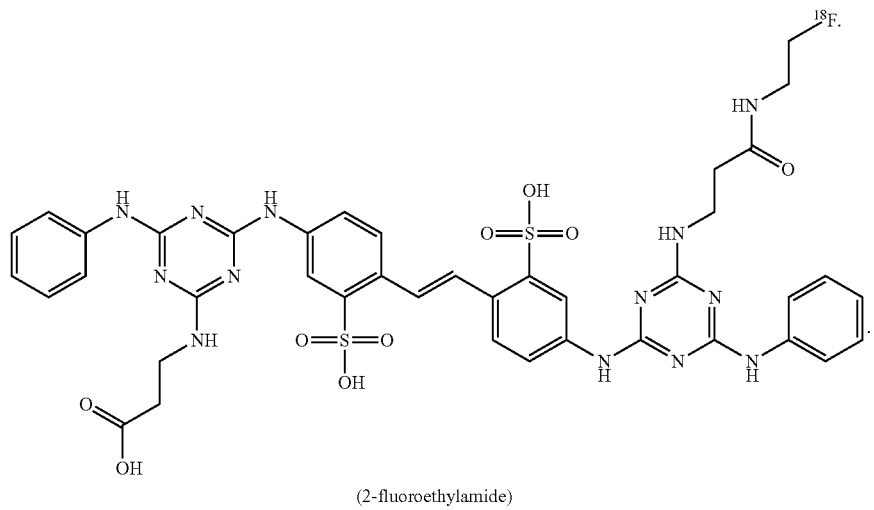

(2-fluoroethylamide)

Compositions are disclosed that include a disclosed compound and a carrier. In some embodiments, a dosage unit is disclosed comprising an effective amount of a disclosed compound and a carrier.

Also disclosed are methods for synthesizing such compounds, such as in racemic forms. The presently disclosed synthetic methods for preparing calcofluor derivatives are particularly facile and thus are uniquely suited to the preparation of $^{18}$F-labeled compounds for PET imaging. Methods are disclosed for using the labeled compounds; for example in positron emission tomography (PET) detection of fungi, such as filamentous fungi, such as *Aspergillus.*

In some embodiments, methods of detecting a fungal infection in a subject are disclosed. These methods can comprise administering a radiologically effective amount of the disclosed to the subject and measuring the radioactivity distribution arising from the administration of the compound to the subject, such as by using positron emission tomography (PET). For example, the amount of radioactive material that is administered is dependent upon the radiation dose to be delivered. In some examples, the fungal infection is a filamentous fungal infection, such as a fungal infection caused by an *Aspergillus* species, such as *A. candidus, A. chevalieri, A. clavatus, A. flavipes, A. flavus, A. fumigatus, A. granulosus, A. nidulans, A. niger, A. parasiticus, A. restrictus, A. sydowii, A. tamari, A. ustus, A. versicolor*, and/or *A. wentii*. In some embodiments, the filamentous fungal infection is mucormycosis, *exserohilum*, or phaeohyphomycosis. In some embodiments, the method further comprises administering an antifungal drug to the subject and assessing an effect of the antifungal drug on fungal activity. In some examples, the radiologically effective amount administered to the subject is from about 1 to about 20 mCi.

Also disclosed are methods of monitoring a fungal infection in a subject which comprise administering a radiologically effective amount of any one of the disclosed compounds to the subject, and measuring the radioactivity arising from the administration of the compound to the subject, thereby monitoring the fungal infection. In some examples, the method is a method of monitoring an *Aspergillus* species infection, mucormycosis, *exserohilum*, or phaeohyphomycosis. In some examples, the method further comprises selecting a subject exhibiting one or more signs or symptoms associated with a fungal infection or a subject known to be at risk of acquiring a fungal infection. In some examples, the method further comprises administering an antifungal drug to the subject and assessing an effect of the antifungal drug on fungal activity. In some examples, assessing the effect of the antifungal drug on fungal activity comprises performing positron emission tomography (PET) of the subject's respiratory tract, gastrointestinal tract, liver, brain or combinations thereof and comparing the activity to a control, such as a reference value or PET prior to administering the antifungal drug, wherein decreased radioactivity relative to a control or PET prior to administering the antifungal drug indicates that the treatment of the fungal infection is effective. In some examples, the method is used to monitor reoccurrence. In some examples, the method is used to monitor pulmonary lung infection or a condition associated with a pulmonary lung infection.

The foregoing and other features and advantages of the disclosure will become more apparent from the following detailed description, which proceeds with reference to the accompanying figures.

DETAILED DESCRIPTION

I. Introduction

Figure 1:
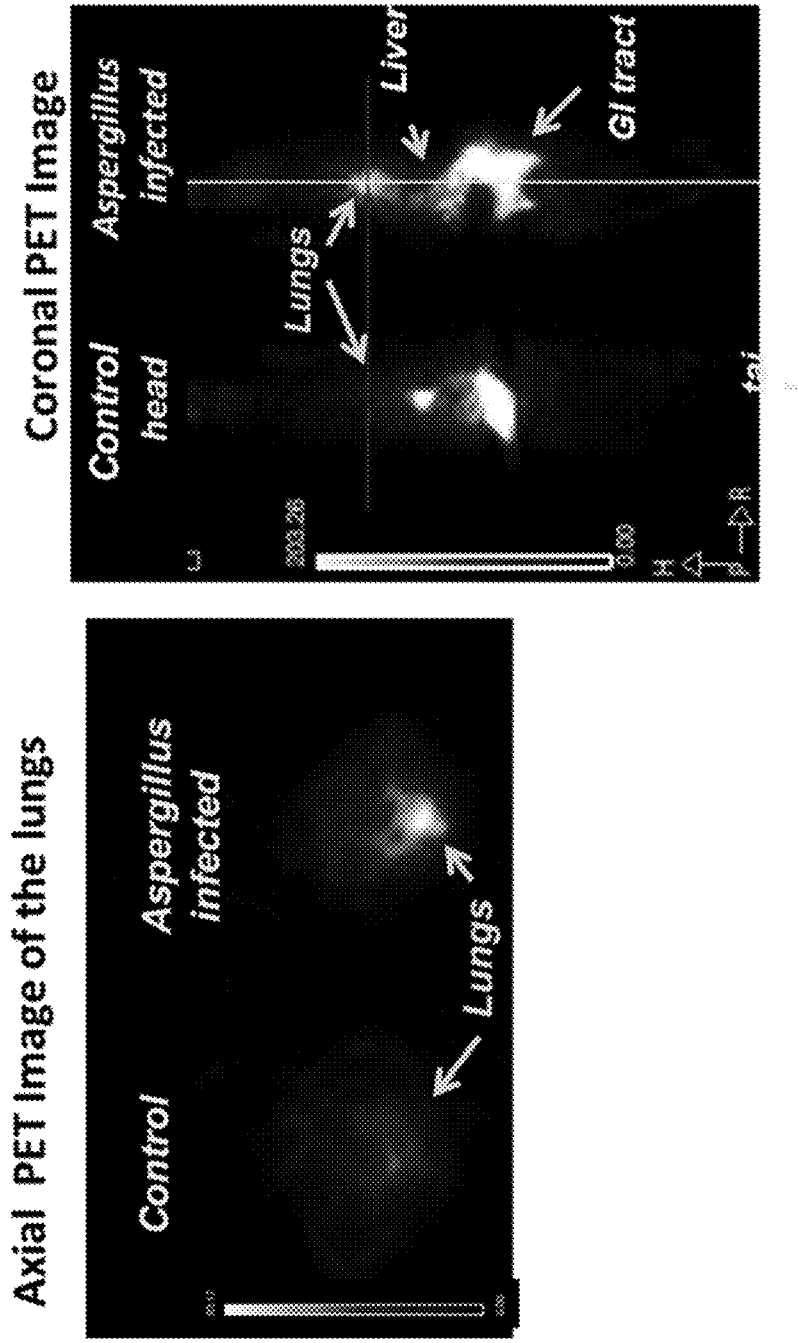
FIG. 1 provides a set of PET images illustrating $^{18}$F-labeled calcofluor derivative uptake in the various tissues in control and *Aspergillus*-infected mice.

Large numbers of patients are at risk for aspergillosis and include those receiving stem cell and solid organ transplants and those immunosuppressed that are neutropenic. Infectious complications are frequent and there is great need to rule out mold infections, such as aspergillosis, because of the high mortality and the need to use toxic antifungals that prevent long courses of empiric therapy. The current state of testing for aspergillosis besides culture of the organism, includes a blood galactomannan test that is commercially available and in current clinical use. However, the sensitivity and specificity is poor due to cross reactivity with plant fibers and it is unable to detect many fungi that do not have galactomannan such as mucormycosis. Other blood tests that have been developed include PCR-based assays, rolling circle amplification (RCA) and loop mediated amplification (LAMP). However, all blood-based methods lack sensitivity and specificity because of cross reactions. Thus, a diagnostic imaging test specific for fungal infections could be very advantageous, even if only a small percentage of patients turn out to have the diagnosis of aspergillosis.

Compounds such as calcofluor can be used for visualizing a broad range of medically relevant fungi under the microscope, due to their specific nature of binding, high level fluorescence (detectable under the microscope) and low binding to patient tissue. Calcofluor is a fairly non-toxic compound that is used to dye clothes, due to its high affinity for cellulose-containing cotton fibers. It has also been used to follow ground water migration due to its fluorescent properties and low toxicity. The present inventors performed studies with calcofluor that showed that the compound, injected into a subject, could be recovered in harvested lung tissue and demonstrated fluorescent fungal hyphal forms under the microscope of lung tissue removed from the subject infected with *Aspergillus.*

As such, the inventors synthesized synthetic calcofluor derivatives that allowed $^{18}$F labeling that would enable the compound to be detected by positron emission tomography (PET) scanning. The compound was next injected into 20 mice infected with *Aspergillus* and 20 control mice and imaged by PET. These studies determined that lungs of mice infected with *Aspergillus* took up 30% more radioactive tracer than uninfected lungs.

Based upon these findings, disclosed herein are $^{18}$F-labeled calcofluor derivatives for PET imaging which are capable of detecting filamentous fungi, such as by binding to chitin within fungal cell walls. Also disclosed herein are methods for using the disclosed compounds, for example to evaluate the presence or status of a fungal infection, such as a filamentous fungal infection, such as aspergillosis. The disclosed imaging methods allow the clinician to evaluate the composition of the specific nodule that prompted the evaluation and to exclude possible non-specific interactions based on whether the detected material superimposes on the nodule of interest.

Specifically, regarding the synthesis of the compounds, synthesis of the material, all analogs disclosed herein were prepared with the same general procedure. A one pot reaction using sequential addition of the components and increasing temperature for each step of the reaction was employed. The desired products were isolated from the reaction mixture by chromatography (described in detail below).

II. Terms

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

Variables such as $R^1$, $R^2$, $R^3$, $R^4$, $Z^1$ and $Z^2$, used throughout the disclosure are the same variables as previously defined unless stated to the contrary.

"Calcofluor" is a compound with the chemical formula $C_{40}H_{42}N_{12}O_{10}S_2Na_2$ and a chemical structure of sional or three dimensional images of the distribution of 18F-FDG within the body. The images can be assessed by a nuclear medicine physician or radiologist to provide diagnoses of various medical conditions.

"Functional group" refers to a specific group of atoms within a molecule that is responsible for the characteristic chemical reactions of the molecule. Exemplary functional groups include, without limitation, alkane, alkene, alkyne, arene, halo (fluoro, chloro, bromo, iodo), epoxide, hydroxyl, carbonyl (ketone), aldehyde, carbonate ester, carboxylate, ether, ester, peroxy, hydroperoxy, carboxamide, amine (primary, secondary, tertiary), ammonium, imide, azide, cyanate, isocyanate, thiocyanate, nitrate, nitrite, nitrile, nitroalkane, nitroso, pyridyl, phosphate, sulfonyl, sulfide, thiol (sulfhydryl), and disulfide.

"Fungus" refers to living, single-celled and multicellular organisms belonging to the kingdom Fungi. Most species are characterized by a lack of chlorophyll and presence of chitinous cell walls, and some fungi may be multinucleated. In some examples, the fungus is a filamentous fungus, which contains chitin in their cell walls and grows as tubular, elonged and thread-like (filamentous) structures. Examples of filamentous fungi, include *Aspergillus* species of fungi, fungi from the order of Mucorales, phaeohyphomycosis, or

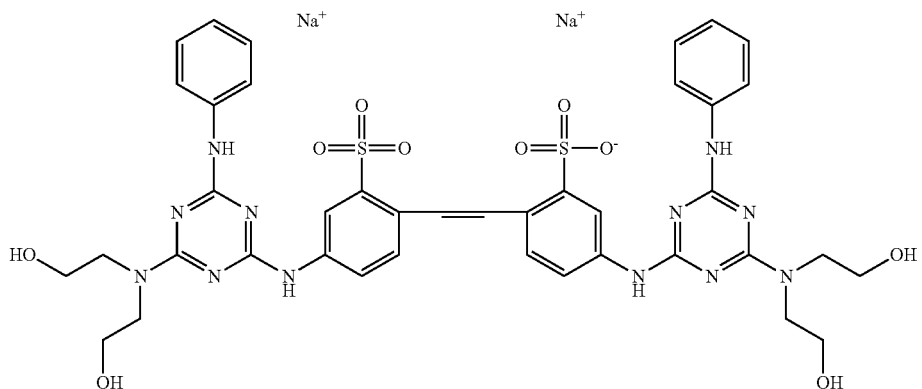

Alternate names include benzenesulfonic acid, 2,2'-(1,2-ethenediyl)bis[5-[[4-[bis(2-hydroxyethyl)amino]-6-(phenylamino)-1,3,5-triazin-2-yl]amino]-, disodium salt. Calcofluor is an optical brightening agent which absorbs UV wavelengths and emits (fluoresces) in the blue to blue-green end of the visible spectrum. Calcofluor is a fairly non-toxic compound that is used to dye clothes, due to its high affinity for cellulose-containing cotton fibers. It has also been used to follow ground water migration due to its fluorescent properties and low toxicity.

"Derivative" refers to a compound or portion of a compound that is derived from or is theoretically derivable from a parent compound. Disclosed herein are isotopically-labeled calcofluor derivatives "18F" or "Fludeoxyglucose" (18F) (INN), or fludeoxyglucose (F18) (USAN), also commonly called fluorodeoxyglucose and abbreviated [18F]FDG, 18F-FDG or FDG, is a radiopharmaceutical used in the medical imaging modality positron emission tomography (PET). Chemically, it is 2-deoxy-2-(18F)fluoro-D-glucose, a glucose analog, with the positron-emitting radioactive isotope fluorine-18 substituted for the normal hydroxyl group at the 2' position in the glucose molecule.

The uptake of 18F-FDG by tissues is a marker for the tissue uptake of glucose, which in turn is closely correlated with certain types of tissue metabolism. After 18F-FDG is injected into a patient, a PET scanner can form two dimen-

*exserohilum*. Any of the disclosed compositions can be used to detect a filamentous (chitin cell wall) fungal infection. In one example, a fungus is an *Aspergillus* species. Representative, non-limiting examples of *Aspergillus* species include *A. candidus, A. chevalieri, A. clavatus, A. flavipes, A. flavus, A. fumigatus, A. granulosus, A. nidulans, A. niger, A. parasiticus, A. restrictus, A. sydowii, A. tamari, A. ustus, A. versicolor*, and *A. wentii*.

In one example, the fungus is *Aspergillus fumigatus* (Af). *Aspergillus fumigatus* is one of the most common *Aspergillus* species to cause disease in individuals with an immunodeficiency. *A. fumigatus*, a saprotroph widespread in nature, is typically found in soil and decaying organic matter, such as compost heaps, where it plays an essential role in carbon and nitrogen recycling. Colonies of the fungus produce from conidiophores thousands of minute grey-green conidia (2-3 μm) that readily become airborne. The fungus is capable of growth at 37° C./99° F., and can grow at temperatures up to 50° C./122° F., with conidia surviving at 70° C./158° F.—conditions it regularly encounters in self-heating compost heaps. Its spores are ubiquitous in the atmosphere. In immunocompromised individuals, such as organ or bone marrow transplant recipients and people with leukemia, the fungus is more likely to become pathogenic, over-running the host's weakened defenses and causing a range of diseases generally termed aspergillosis.

In some examples, an "*Aspergillus*-associated condition or disease" is one which is associated with aspergillosis, including, but not limited to invasive aspergillosis (IA). Invasive aspergillosis is an opportunistic fungal infection caused mainly by *Aspergillus fumigatus* (Af). Invasive aspergillosis normally only occurs in severely immune-compromised patients and has a high mortality rate (25-90%). Invasive disease is most commonly seen in the lungs, which is called pulmonary aspergillosis, but although less common, dissemination of *aspergillus* to other tissues, including the central nervous system, sinuses, bone, heart, kidney, eye, blood and skin, has been reported. Risk factors for invasive aspergillosis include patients on steroids, chemotherapy treatment resulting in severe neutropenia, stem cell and solid organ transplantation, later stages of AIDS, and a genetic disease called chronic granulomatous disease.

Disclosed herein are methods for detecting invasive aspergillosis and/or for monitoring the treatment of invasive aspergillosis.

In some examples, the filamentous fungus is in the order of Mucorales. For example, in some embodiments the disclosed derivatives are used to diagnose mucormycosis or determine the efficacy of a treatment of mucormycosis. Mucormycosis is any fungal infection caused by fungi in the order Mucorales. Generally, species in the *Mucor, Rhizopus, Absidia*, and *Cunninghamella* genera are most often implicated. This disease is often characterized by hyphae growing in and around vessels.

In some examples, the filamentous fungus is *exserohilum* and the disclosed derivatives and methods are used to diagnose an *exserohilum* infection. *Exserohilum* is a common mold found in soil and on plants, especially grasses, and it thrives in warm and humid climates. In some particular examples, the disclosed compounds and methods are used to diagnosis a subject with an *exserohilum rostratum* infection.

In some examples, the filamentous fungus is phaeohyphomycosis which is a heterogeneous group of mycotic infections caused by dematiaceous fungi whose morphologic characteristics in tissue include hyphae, yeast-like cells, or a combination of these. In these examples, the disclosed compositions and methods are used to diagnose a subject with phaeohyphomycosis infection and/or determine the efficacy of a treatment of phaeohyphomycosis.

"Optional" or "optionally" means that the subsequently described event or circumstance can but need not occur, and that the description includes instances where said event or circumstance occurs and instances where it does not.

The term "subject" includes both human and veterinary subjects.

The term "aliphatic group" is defined as including alkyl, alkenyl, alkynyl, halogenated alkyl and cycloalkyl groups as described above. A "lower aliphatic" group is a branched or unbranched aliphatic group having from 1 to 10 carbon atoms.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched aliphatic hydrocarbon having from 1 to 10 carbon atoms.

The term "aryl group" refers to any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxyl, carboxylic acid, or alkoxy, or the aryl group can be unsubstituted. The term "alkyl amino" refers to alkyl groups as defined above where at least one hydrogen atom is replaced with an amino group.

The term "hydroxyl group" is represented by the formula —OH. The term "alkoxy group" is represented by the formula —OR, where R can be an alkyl group, optionally substituted with an alkenyl, alkynyl, aryl, aralkyl, cycloalkyl, halogenated alkyl, or heterocycloalkyl group as described above.

The term "hydroxyalkyl group" refers to an alkyl group that has at least one hydrogen atom substituted with a hydroxyl group. The term "alkoxyalkyl group" is defined as an alkyl group that has at least one hydrogen atom substituted with an alkoxy group described above. Where applicable, the alkyl portion of a hydroxyalkyl group or an alkoxyalkyl group can have aryl, aralkyl, halogen, hydroxyl and/or alkoxy substituents.

The term "amine group" is represented by the formula —NRR', where R and R' can be, independently, hydrogen or an alkyl, alkenyl, alkynyl, aryl, aralkyl, cycloalkyl, halogenated alkyl, or heterocycloalkyl group described above.

The term "amide group" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above.

The term "aralkyl" refers to an aryl group having an alkyl group, as defined above, attached to the aryl group. Examples aralkyl groups include, without limitation, benzyl groups and trityl groups.

The terms "halogenated alkyl" or "haloalkyl group" refer to an alkyl group as defined above with one or more hydrogen atoms present on these groups substituted with a halogen (F, Cl, Br, I).

Optionally substituted groups, such as "substituted alkyl," refers to groups, such as an alkyl group, having from 1-5 substituents, typically from 1-3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, optionally substituted heteroaryl, optionally substituted heterocyclyl, hydroxyl, thiol and thioalkoxy.

As used herein, unless otherwise noted, the term "leaving group" refers to a charged or uncharged substituent group on an activated compound which leaves during a substitution, displacement and/or elimination reaction. Suitable examples include, without limitation, halides, such as —Cl, —Br and —I and sulfonates, such as —S(O)$_2$R, wherein R is, for example a lower alkyl, haloalkyl or aryl group.

The term "pharmaceutically acceptable salt or prodrug" is used throughout the specification to describe any pharmaceutically acceptable form (e.g., ester, phosphate ester, salt of an ester or a related group) of an inhibitor compound, which, upon administration to a subject, provides or produces an active compound.

The disclosed compounds also encompass salts including, if several salt-forming groups are present, mixed salts and/or internal salts. The salts are generally pharmaceutically-acceptable salts that are nontoxic or substantially nontoxic to a subject. Pharmaceutically acceptable salts include those derived from pharmaceutically acceptable inorganic or organic bases and acids. In particular, suitable salts include those derived from alkali metals such as potassium and sodium, alkaline earth metals such as calcium and magnesium, among numerous other acids well known in the pharmaceutical art. Examples of salt-forming acidic groups include, but are not limited to, a carboxyl group, a phosphonic acid group or a boronic acid group, that can form salts with suitable bases. These salts can include, for example, nontoxic metal cations which are derived from metals of groups IA, IB, IIA and IIB of the periodic table of the elements. In one embodiment, alkali metal cations such as lithium, sodium or potassium ions, or alkaline earth metal cations such as magnesium or calcium ions can be used. The salt can also be a zinc or an ammonium cation. The salt can also be formed with suitable organic amines, such as unsubstituted or hydroxyl-substituted mono-, di- or tri-alkylamines, in particular mono-, di- or tri-alkylamines, or with quaternary ammonium compounds, for example with N-methyl-N-ethylamine, diethylamine, triethylamine, mono-, bis- or tris-(2-hydroxy-lower alkyl)amines, such as mono-, bis- or tris-(2-hydroxyethyl)amine, 2-hydroxy-tert-butylamine or tris(hydroxymethyl)methylamine, N,N-dilower alkyl-N-(hydroxy-lower alkyl)amines, such as N,N-dimethyl-N-(2-hydroxyethyl)amine or tri-(2-hydroxyethyl)amine, or N-methyl-D-glucamine, or quaternary ammonium compounds such as tetrabutylammonium salts.

Particular compounds possess at least one basic group that can form acid-base salts with inorganic acids. Examples of basic groups include, but are not limited to, an amino group or imino group. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid. For additional examples of "pharmacologically acceptable salts," see Berge et al., *J. Pharm. Sci.* 66:1 (1977).

Pharmaceutically acceptable prodrugs refer to compounds that are metabolized, for example, hydrolyzed or oxidized, in the subject to form a compound of the present disclosure. Typical examples of prodrugs include compounds that have one or more biologically labile protecting groups on or otherwise blocking a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The term "prodrug" also is intended to include any covalently bonded carriers that release an active parent drug of the present invention in vivo when the prodrug is administered to a subject. Since prodrugs often have enhanced properties relative to the active agent pharmaceutical, such as solubility and bioavailability, the compounds disclosed herein can be delivered in prodrug form. Thus, also contemplated are prodrugs of the presently claimed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compound also are contemplated. A variety of suitable protecting groups for use with the disclosed compounds are disclosed in Greene and Wuts; Protective Groups in Organic Synthesis; 3rd Ed.; John Wiley & Sons, New York, 1999.

In general, protecting groups are removed under conditions which will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxyl functional groups is trityl. Other conventional protecting groups are known, and suitable protecting groups can be selected by those of skill in the art in consultation with Greene and Wuts; Protective Groups in Organic Synthesis; 3rd Ed.; John Wiley & Sons, New York, 1999.

When an amine is deprotected, the resulting salt can readily be neutralized to yield the free amine. Similarly, when an acid moiety, such as a phosphonic acid moiety is unveiled, the compound may be isolated as the acid compound or as a salt thereof.

It is understood that substituents and substitution patterns of the compounds described herein can be selected to provide compounds that are chemically stable and that can be readily synthesized by techniques methods set forth in this disclosure. Reference will now be made in detail to the presently preferred compounds.

III. Isotopically-Labeled Calcofluor Derivatives

Certain embodiments of the disclosed, isotopically-labeled calcofluor derivatives are $^{18}$F-labeled calcofluor derivatives. Fluorine has several isotopes in addition to $^{18}$F, all of which are unstable, but only one of these has practical significance: the isotope, $^{18}$F, which is radioactive and has the longest half-life of the unstable isotopes (the other unstable isotopes have half-lives lasting less than 3 minutes). $^{18}$F isotope has a half-life of 110 minutes and is very useful in biological studies and in medicine, but a half-life of less than 2 hours does impose some limits on its utility. Examples of the uses of $^{18}$F include non-invasive measurement of pharmacokinetic phenomena and the localization of tumors with $^{18}$F-labeled 2-fluoro-2-deoxyglucose (e.g. by positron emission tomography).

In any method in which an F-labeled compound is used, it is generally necessary that its physiological properties (e.g. its properties as a substrate for an enzyme) be similar to the endogenous, non-fluorinated compound it is supposed to mimic. The fluorine atom has the advantage of being fairly small in its covalent radius and hence does not differ too markedly from hydrogen in terms of steric hindrance. A fluorine substituent does differ from other substituents in terms of charge density, due to its high electronegativity and electronic density.

Disclosed herein are $^{18}$F-labeled compounds that can be prepared efficiently and used to image fungi (such as filamentous fungi, e.g., *Aspergillus*) and in particular, to evaluate the presence or absences of fungal infection.

Certain disclosed labeled calcofluor derivatives have the structure

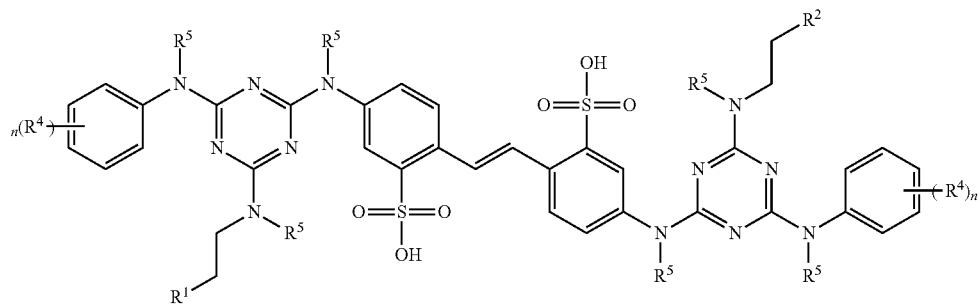

wherein $R^1$ is an amine, a hydroxyl group, a sulfide, a carboxylic acid, an amide, an alkyl, or aryl; $R^2$ is —NHC(O)—$R^3$-L or —C(O)NH—$R^3$-L, wherein $R^3$ is an aryl or an aliphatic group (such as alkyl); each $R^4$ independently may be selected from halogen, aliphatic (such as alkyl), aryl, amine, hydroxyl, haloalkyl, carboxylic acid, amide, aralkyl, cyano, ester, thiol, thioether, or alkoxy; each $R^5$ independently may be selected from hydrogen, aralkyl, alkyl, or aryl, with any one of the aralkyl, alkyl, or aryl groups optionally being substituted with any one of the substituents provided for $R^4$; each n independently is 1, 2, 3, 4, or 5; and L is $^{18}$F or a chelator capable of chelating a radiolabel (such as chelators for [$^{18}$F]AlF, $^{64}$Cu, $^{68}$Ga), 1,4,7,10-tetraazacyclododecane-tetraacetic acid (DOTA) or 1,4,7-triazacyclononane-triacetic acid (NOTA). In some particular embodiments, L is $^{18}$F.

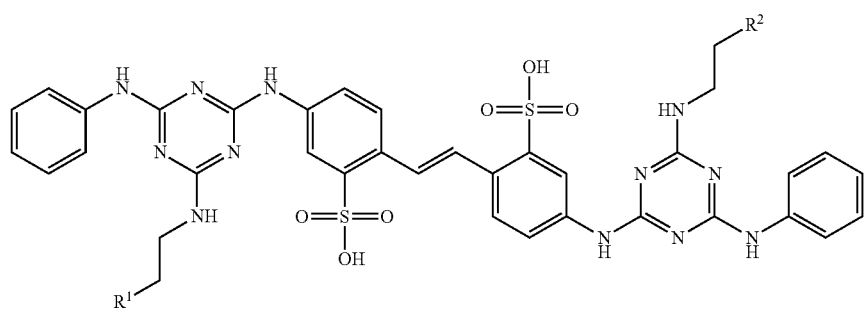

wherein $R^1$, $R^2$, and L are as provided above. In particular disclosed embodiments, $R^2$ is —NHC(O)—$R^3$-L or —C(O)NH—$R^3$-L, wherein $R^3$ is an aryl group comprising an L group in any position on the ring. For example, L may be located in the ortho position, the mew position, the para position, or combinations thereof. In some embodiments wherein $R^3$ is an aryl group, the aryl group may comprise one or more additional substituents, selected from halogen, aliphatic (such as alkyl), aryl, amine, hydroxyl, haloalkyl, carboxylic acid, amide, aralkyl, cyano, ester, thiol, thioether, or alkoxy.

Exemplary embodiments are provided below.

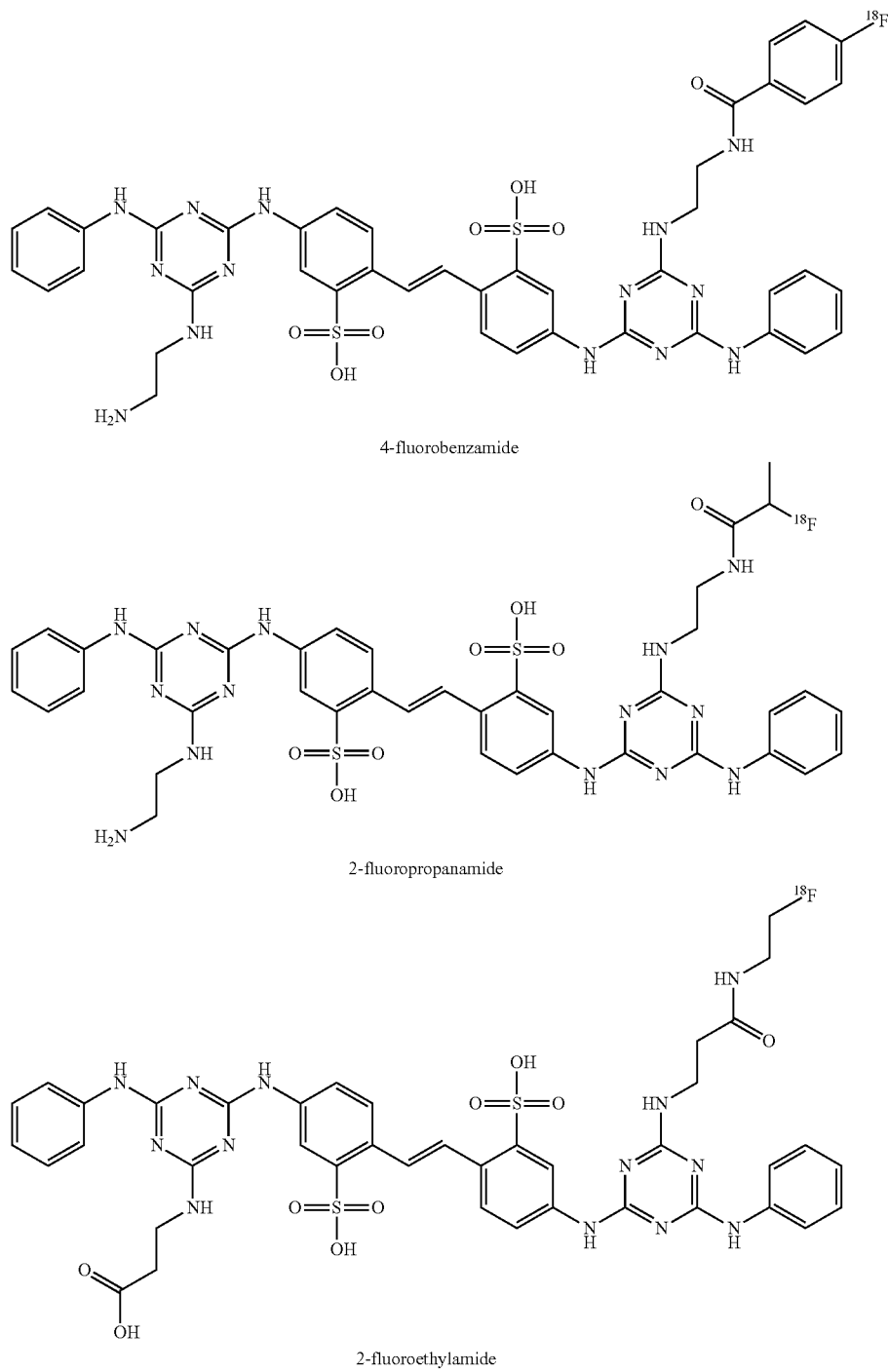

4-fluorobenzamide 2-fluoropropanamide 2-fluoroethylamide

The foregoing compounds include an asymmetric center; thus these compounds can exist in two stereoisomeric forms, termed enantiomers. Thus, compounds and compositions may be provided as individual pure enantiomers or as stereoisomeric mixtures, including racemic mixtures. In certain embodiments the compounds disclosed herein are synthesized in or are purified to be in substantially enantiopure form, such as greater than in a 90% enantiomeric excess, including between a 90% to 95% enantiomeric excess, a 95% to 99% enantiomeric excess, for example, a 95% enantiomeric excess, a 96% enantiomeric excess, a 97% enantiomeric excess, a 98% enantiomeric excess, a 99% enantiomeric excess, or even in greater than a 99% enantiomeric excess, such as in enantiopure form.

IV. Methods for Synthesizing Labeled Compounds

The short half-life of the $^{18}$F isotope can impose severe requirements upon methods for synthesizing the $^{18}$F-labeled compound. The yield of labeled compound should be high, and, even more important, the synthesis must be very rapid so that a significant $^{18}$F isotope concentration remains. All compounds disclosed herein were prepared by following the same general procedure. A one pot reaction using sequential addition of the components and increasing temperature for each step of the reaction was employed. The desired products were isolated from the reaction mixture by chromatography. The chemical synthesis procedures disclosed in Chinese Patent No. CN101298438 are hereby incorporated by reference in their entirety.

Synthesis of the disclosed compounds is depicted in the following Schemes. Scheme 1 illustrates the first two chemical steps taken to synthesize disclosed compounds.

In Scheme 1, cyanuric acid is treated with sodium carbonate and aniline at room temperature overnight. The following day a solution of 10% $Na_2CO_3$ is added along with 4,4-diamino-2,2'disulfonate stilbene. This is heated at 55° C. for 4 hours. At this point the synthesis deviates depending on the compound synthesized.

In one embodiment of the synthesis of a disclosed amino analog (1, Scheme 2), ethylene diamine is added in stoichiometric excess, additional $Na_2CO_3$ is added and the mixture heated at 95° C. overnight. The reaction is cooled, diluted with water and strongly acidified. The precipitate is

SCHEME 1

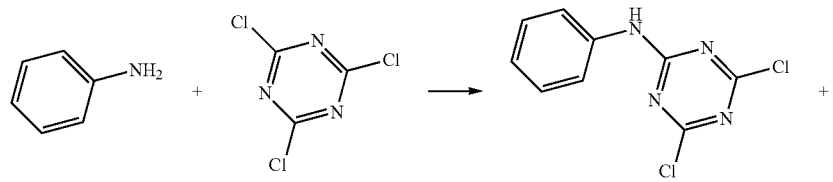

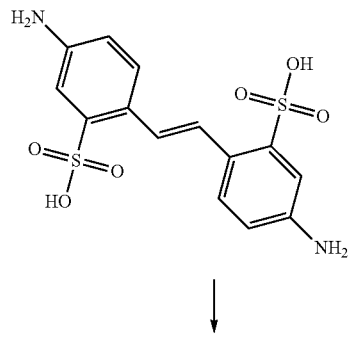

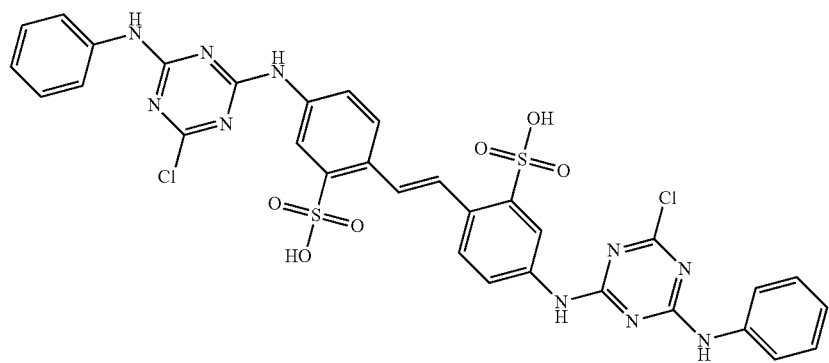

collected by centrifugation. The resulting solid is subject to purification by C-18 chromatography. Two products are isolated; the desired bis amino calcofluor analog and a dimeric structure formed by intermolecular reaction of the intermediates.
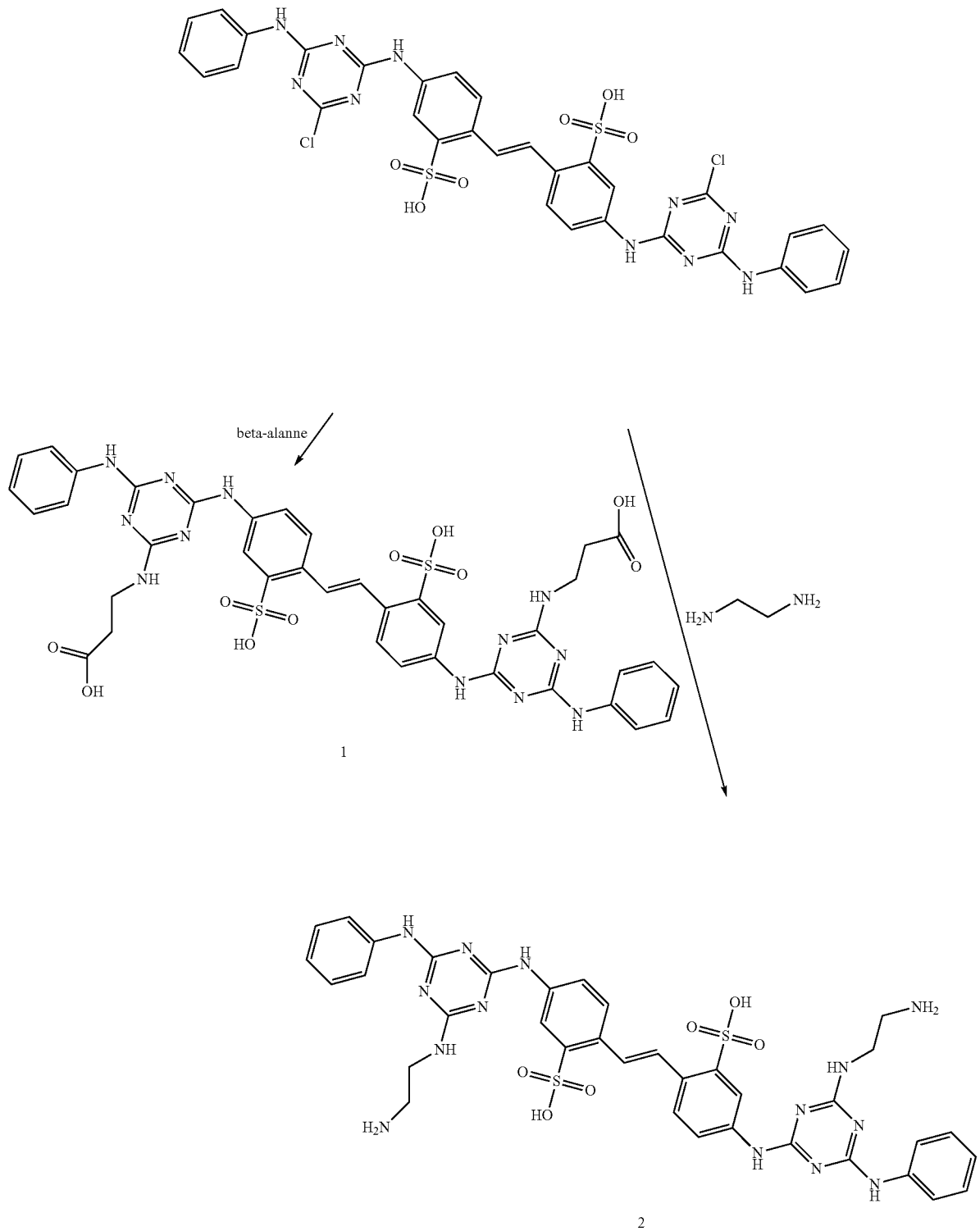
SCHEME 2

In one embodiment of the synthesis of a disclosed di-carboxylic acid (2, scheme 2) analog, beta-alanine is added, additional 10% $Na_2CO_3$, and the reaction heated at 95° C. overnight. The mixture is cooled and acidified. The resulting precipitate is recovered from centrifugation and triturated with acetonitrile. The desired bis-carboxylic acid analog of calcofluor was isolated by C-18 chromatography.

In some embodiments, amide analogs of the above intermediates are prepared. For example, the bis-carboxylic acid analog, 1, is converted into mono and bis-fluoroethylamides by reaction with fluoroethylamine in presence of a standard coupling reagent, pyBOP (Scheme 3).

SCHEME 3

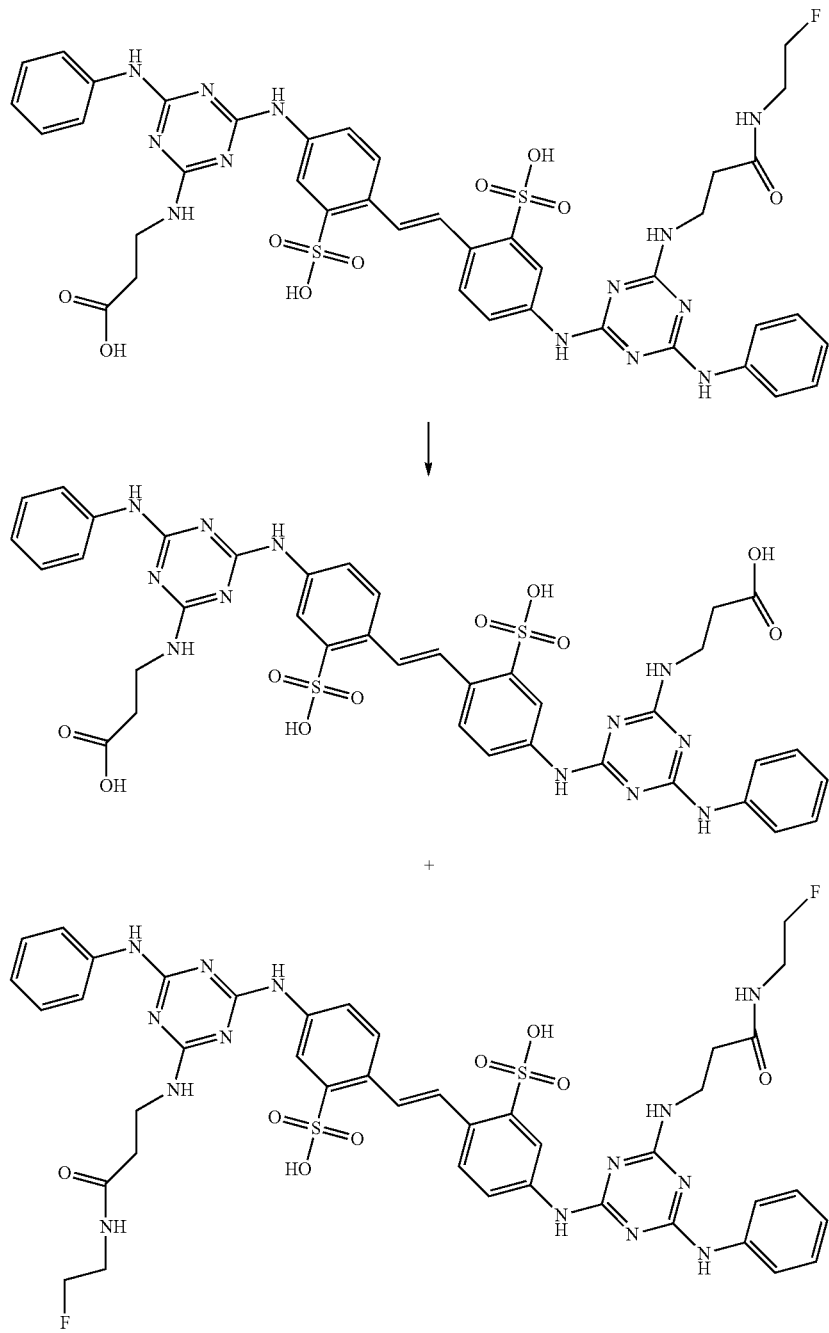

Scheme 4 depicts the bis-amine analog (2) being converted to bis- and mono-amides. Reaction of (2) with p-nitrophenyl 2-fluoropropionate provides disclosed 2-fluoropropyl amides (Scheme 4).
SCHEME 4
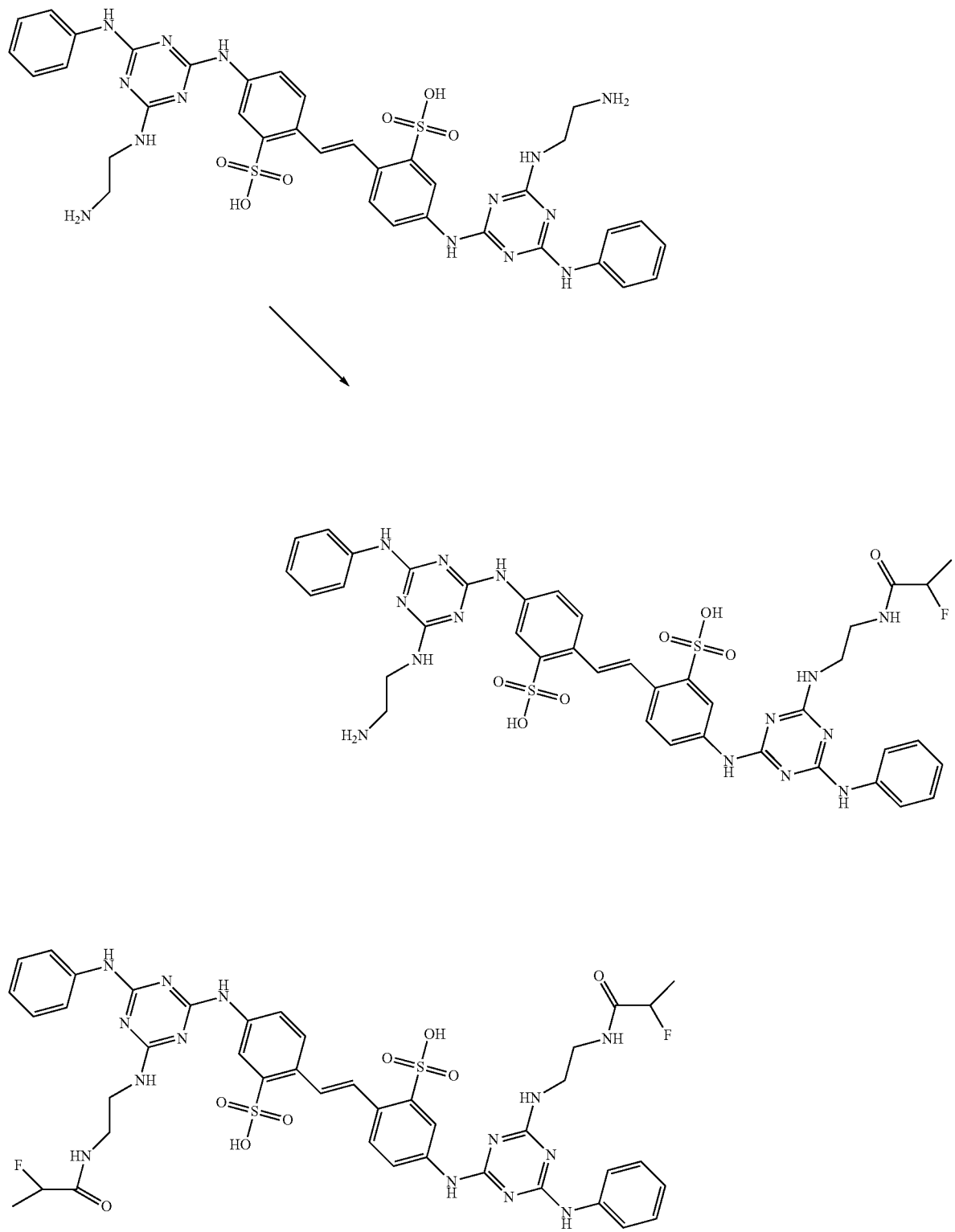

Treatment with N-hydroxysuccinimidyl 4-fluorobenzoate (SFB) provides disclosed 4-fluorobenzamides (Scheme 5).

SCHEME 5

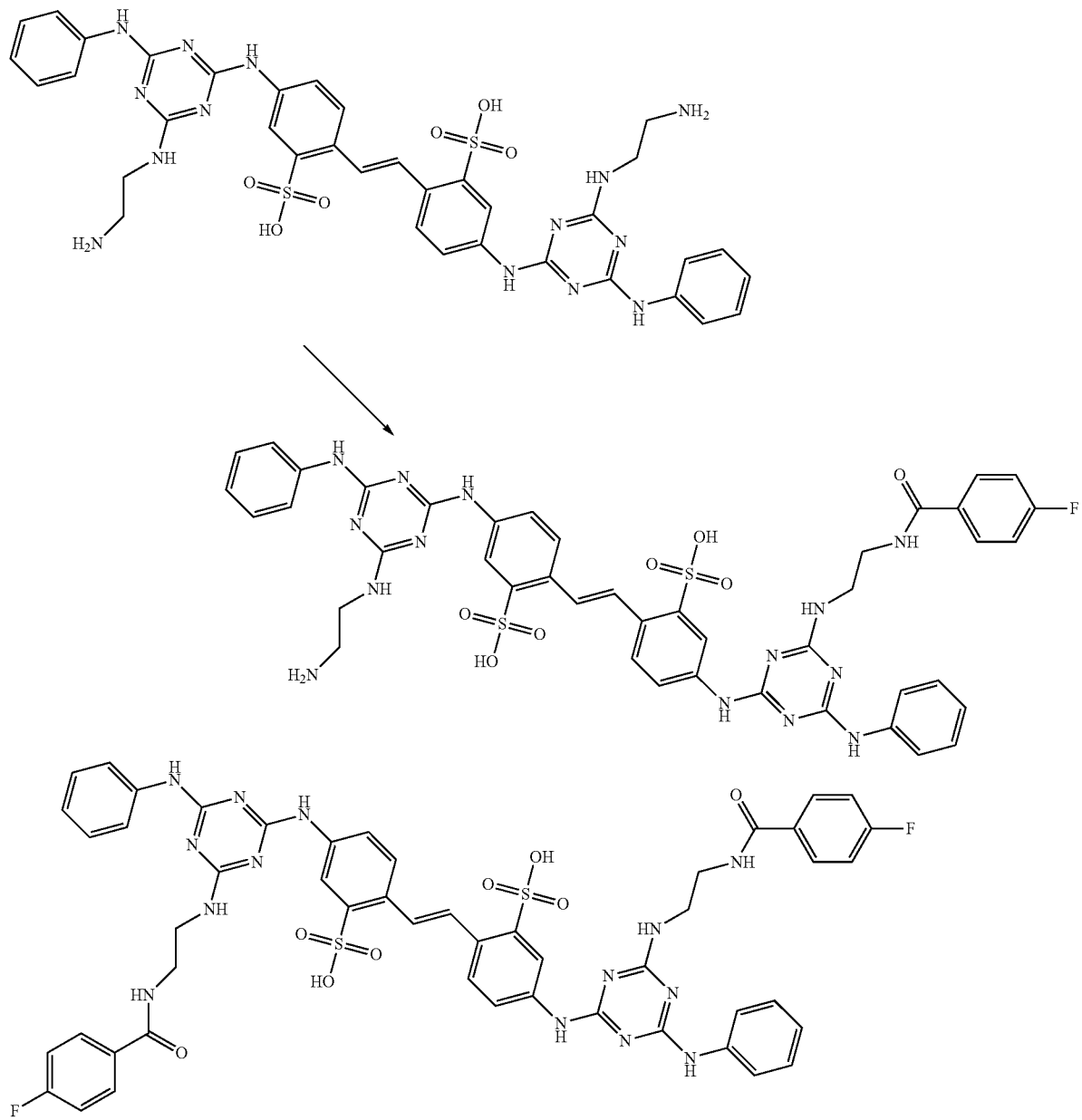

Radiochemical synthesis of 4-nitrophenyl 2-[18F]fluoropropionate and N-hydroysuccinimidoyl 4-[18F]fluorobenzoate can be prepared by methods known to those of skill in the art. The radiolabeling required the synthesis of one of these prosthetic groups and coupling to the amino functional group of compound (2). In one embodiment, this is accomplished by heating a DMF solution of the prosthetic group, compound (2) and diisopropyl ethyl amine. Radiolabeled products can be isolated by preparative HPLC. It is contemplated that fluoroethyl amide version from compound (1) and other amide linked radiolabeling methods, including attachment of chelators, such as DOTA or NOTA, for [18F]AlF, Cu-64, Ga-68, etc. can be prepared.

V. Compositions, Administration and Use of the Disclosed Compounds

Disclosed herein are methods for using the disclosed radioactive, isotopically-labeled calcofluor derivatives in a noninvasive assay to detect and assess, for example, fungi, including filamentous fungi, such as *Aspergillus*, in particular tissues, such as a subject's respiratory tract (such as nose and nasal passages, paranasal sinuses, pharynx, larynx, trachea, bronchi, and bronchioles, lungs), gastrointestinal tract, liver, brain tissue or cells or combinations thereof. The disclosed methods are useful for evaluating the presence of a fungal infection, such as infection with filamentous fungi, such as an *Aspergillus* species, such as *A. candidus, A. chevalieri, A. clavatus, A. flavipes, A. flavus, A. fumigatus, A. granulosus, A. nidulans, A. niger, A. parasiticus, A. restrictus, A. sydowii, A. tamari, A. ustus, A. versicolor,* and/or *A. wentii*. In one example, the disclosed method is used to detect *Aspergillus fumigatus* (Af). *Aspergillus fumigatus* is one of the most common *Aspergillus* species to cause disease in individuals with an immunodeficiency. In some examples, the disclosed methods are used to diagnosis a subject with aspergillosis. In some examples, the disclosed methods are used to monitor the efficacy of treatment of a subject with aspergillosis. In some examples, the disclosed methods are used to diagnosis a subject with filamentous fungal infections, including, but not limited to mucormycosis, phaeohyphomycosis, or *exserohilum*. In some examples, the disclosed methods are used to diagnosis a subject with any fungal infection caused by fungi capable of binding to a disclosed calcofluor derivative. In some examples, the disclosed methods are used to monitor the efficacy of treatment of a subject with filamentous fungus, such as mucormycosis, phaeohyphomycosis, or *exserohilum*.

In some embodiments of the disclosed noninvasive method/assay, the subject is administered a disclosed compound and typically the compound is allowed to partially clear from the subject and to be taken up preferentially by fungal-infected tissues (such as respiratory tract, gastrointestinal tract, liver, brain tissue or cells) and then a portion of the subject containing the tissue of interest is analyzed non-invasively by positron emission tomography (PET). A proportion of the compound will remain in the body, bound to fungus or associated with fungal-infected cells. Because of the short half-life of radioactive $^{18}$F (110 minutes), a compromise is reached between having the maximum clearance providing the best signal:noise ratio, and having enough signal to provide adequate image resolution. One method for quantitative PET imaging is described by Yao et al. *J. Nucl. Med.* 1995, 36, 794-799, which is incorporated herein by reference in its entirety. Additional methods are known to those of skill in the art and are taught by Wahl, "Regions of Interest in the Venous Sinuses as Input Functions for Quantitative PET," *J. Nucl. Med.* 1999, 40 1666-1675; and Fowler, J. S. et al. "PET and Drug Research and Development," *J. Nucl. Med.* 1999, 40, 1154-1163. The Wahl and Fowler references also are incorporated herein by reference in their entirety.

In one embodiment, the disclosed compounds can be used to determine the severity of fungal infection in a subject. For example, the disclosed compounds can be used to directly measure fungi presence in particular tissues, which has marked advantages over simply measuring plasma levels. Because PET imaging of the disclosed compounds can be used to detect fungi in vivo, the compounds can be used to test the efficacy of putative antifungal therapies, including therapies for aspergillosis (e.g., invasive aspergillosis).

The disclosed compounds can be administered to any subject who is known to be or is suspected or at risk of being infected with a fungus. Fungal infections to be assessed using the disclosed isotopically labeled compounds include infections associated with immunosuppressed subjects, such as subjects undergoing chemotherapy, organ transplant, or afflicted with an autoimmune disorder or disease, such as HIV. In particular examples the fungal infection is filamentous fungal infection, such as of an *Aspergillus* species, such as *A. candidus, A. chevalieri, A. clavatus, A. flavipes, A. flavus, A. fumigatus, A. granulosus, A. nidulans, A. niger, A. parasiticus, A. restrictus, A. sydowii, A. tamari, A. ustus, A. versicolor,* and/or *A. wentii*.

The present compounds also can be used in the assessment of the response of a subject to therapeutic interventions using PET scanning or another external radiation detection technique. The subject can be scanned at more than one time and the data from two or more scans may be compared to determine potential differences in the uptake and/or localization of the inhibitor compound. Comparisons can involve either qualitative image comparison (e.g., contrast of uptake from background) or quantitative indices derived from the imaging or external radiation detection data (e.g. standardized uptake values (SUVs)). A decrease in total radioactive signal (beyond that due to radioactive decay) indicates reduced fungal activity associated with drug activity, whereas an increase in total radioactive signal (after adjusting for decay), indicates a less effective drug. Moreover, the efficacy of the drug can be assessed on an organ or tissue specific basis by monitoring the radioactive signal from specific tissues. Of specific interest is the effect of drugs on fungal sanctuaries, such as the respiratory tract, gastrointestinal tract, liver, and/or brain, wherein reduced positron emissions from one or more of these tissues indicates that the drug being evaluated is effective at reducing fungal activity in such tissues.

In one embodiment, the disclosed labeled compounds optionally are employed in combination with other therapeutic agents for the assessment or monitoring of the effect of such therapeutic agents on the infections or conditions indicated above. Examples of such further therapeutic agents include agents that are effective for the treatment or prophylaxis of fungal infections these include, without limitation, polyene antifungal agents (e.g., amphotericin B, candicidin, filipin, hamycin, natamycin, nystatin and rimocidin), imidazole antifungal agents (e.g., bifonazole, butoconazole, clotrimazole, econazole, fenticonazole, isoconazole, ketoconazole, miconazole, omoconazole, oxiconazole, sertaconazole, sulconazole, and tioconazole), triazole antifungal agents (e.g., albaconazole, fluconazole, isavuconazole, itraconazole, posaconazole, ravuconazole, terconazole and voriconazole), thiazole antifungal agents (e.g., abafungin), allylamines (e.g., amorolfin, butenafine, naftifine and terbinafine), echinocandins (e.g., anidulafungin, caspofungin and micafungin) and/or other antifungal agents (such as benzoic acid, ciclopirox olamine, griseofulvin, 5-fluorocytosine, tolnaftate, and undecylenic acid).

The present analogues can also be used in the assessment or staging of fungal infection based on quantitative or qualitative measurements of uptake of the present analogues by tissue. The tissue uptake of the analogue can be determined while the tissue is within the body or outside the body. The uptake measurements can be performed in conjunction with pathologic/histologic/histochemical/immunohistochemical assessment of the same tissue for classification and evaluation of infection. In one aspect, the method disclosed can be used to determine the degree of infection of a tissue by quantitating the amount of $^{18}$F radioactivity present.

The disclosed methods of the present disclosure are valuable tools for practicing physicians to make quick treatment decisions for a fungal infection, such as a filamentous fungal infection, including an *Aspergillus* species-associated condition/disease, such as aspergillosis, including IA. These treatment decisions can include the administration of antifungal agents (e.g., anti-*Aspergillus* species agent(s)) and decisions to monitor a subject for onset and/or advancement of a fungal infection, such as an *Aspergillus* species-associated condition. The method disclosed herein can also be used to monitor the effectiveness of a therapy. In some examples, monitoring is performed by a clinical healthcare provider.

Following the measuring of the radioactivity arising from the administration of a disclosed compound to the subject, the assay results, findings, diagnoses, predictions and/or treatment recommendations are typically recorded and communicated to technicians, physicians and/or patients, for example. In certain embodiments, computers will be used to communicate such information to interested parties, such as, patients and/or the attending physicians. Based on the measurement, the therapy administered to a subject can be modified or started (in the case of monitoring for a relapse).

In one embodiment, a diagnosis, prediction and/or treatment recommendation based on the radioactivity level detected in a test subject is communicated to the subject as soon as possible after the assay is completed and the diagnosis and/or prediction is generated. The results and/or related information may be communicated to the subject by the subject's treating physician. Alternatively, the results may be communicated directly to a test subject by any means of communication, including writing, such as by providing a written report, electronic forms of communication, such as email, or telephone. Communication may be facilitated by use of a computer, such as in case of email communications. In certain embodiments, the communication containing results of a diagnostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present disclosure is not limited to methods which utilize this particular communications system. In certain embodiments of the methods of the disclosure, all or some of the method steps, including the assaying of samples, diagnosing of diseases, and communicating of assay results or diagnoses, may be carried out in diverse (e.g., foreign) jurisdictions.

In several embodiments, identification of a subject as having a fungal infection, (e.g., a filamentous fungal infection) such as an *Aspergillus* species-associated condition, results in the physician treating the subject, such as prescribing one or more therapeutic agents for inhibiting or delaying one or more signs and symptoms associated with the fungal infection (e.g., *Aspergillus* species-associated disorder/condition). In additional embodiments, the dose or dosing regimen is modified based on the information obtained using the methods disclosed herein.

The subject can be monitored while undergoing treatment using the methods described herein in order to assess the efficacy of the treatment protocol. In this manner, the length of time or the amount given to the subject can be modified based on the results obtained using the methods disclosed herein. The subject can also be monitored after the treatment using the methods described herein to monitor for relapse. In this manner, whether to resume treatment can be decided based on the results obtained using the methods disclosed herein.

The present compounds also can be used in the anatomical mapping of the distribution of fungi in the body using PET or another external radiation detection technique in combination with anatomical images obtained using CT, MRI, and/or ultrasound. The anatomical images can be acquired using a dedicated CT/PET, MRI/PET, PET/ultrasound scanning device or separate PET and CT/MRI/ultrasound scanning devices. If separate PET and CT/MRI/ultrasound imaging devices are used, image analysis techniques can be employed to spatially register the PET images with the anatomical images. The method can be used for intraorgan mapping of fungal localization.

In alternative embodiments, the disclosed compounds also can be used in radiolabeling of fungus and in vitro counting of radioactivity. The tracer can be administered in vivo or ex vivo in tissue or cell culture experimental models.

Another aspect of the disclosure includes compositions prepared for administration to a subject and which includes a diagnostically effective amount of one or more of the currently disclosed compounds. An effective amount of a disclosed compound will depend on the route of administration, the species of subject and the physical characteristics of the subject being treated or evaluated. Specific factors that can be taken into account include disease severity and stage, weight, diet and concurrent medications. The relationship of these factors to determining a therapeutically or radiologically effective amount of the disclosed compounds is understood by those of skill in the art. For example, a main factor in determining an effective amount is the desired radiation dose to the target tissue/cells. Exemplary radiation guidelines for particular tissues/cells are available by the Food and Drug Administration (FDA). In general, the mass dose is not increased above the no-carrier added amount. For example, injected mass is microgram amounts per subject. In some examples, a suitable dose for consideration will be in the range of analogous compounds, taking into account differences in potency in in vitro testing, generally from about 0.001 to 400 mg per kilogram body weight of the subject per dose, such as in a range between about 0.01 mg and about 250 mg/kg/dose, for example in the range 0.5 to 50 mg per kilogram body weight per dose or in the range 1 to 300 mg per kilogram body weight per dose. The presently disclosed isotopically labeled compounds may be administered in dosage unit formulations containing conventional non-toxic pharmaceutically acceptable carriers, adjuvants and vehicles.

Compositions for administration to a subject can include carriers, thickeners, diluents, buffers, preservatives, surface active agents in addition to the molecule of choice. Compositions can also include one or more active ingredients such as antimicrobial agents, anti-inflammatory agents, anesthetics, and the like. Pharmaceutical formulations can include additional components, such as carriers. Pharmaceutically acceptable carriers which may be useful for these formulations are provided in Remington's Pharmaceutical Sciences, by E. W. Martin, Mack Publishing Co., Easton, Pa., 19th Edition (1995).

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. In some examples, ethanol is added for increasing solubility, such as up to 10% ethanol. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In some examples, the carrier is a non-natural agent.

In particular disclosed embodiments, the composition may further comprise one or more additional components, such as a pharmaceutically acceptable carrier (e.g., water, saline, aqueous dextrose, glycerol, and/or ethanol), a pharmaceutically acceptable excipient, an emulsifier, a flavoring, a lubricant, a solubilizer, a sweetener, or combinations thereof. In addition to biologically-neutral carriers, pharmaceutical compositions that are disclosed herein can contain minor amounts (e.g., greater than 0% to less than about 10%, about 9%, about 8%, about 7%, about 6%, or less than about 5%) of non-toxic auxiliary substances, such as wetting or emulsifying agents, preservatives, and pH buffering agents and the like. For example, some composition embodiments disclosed herein can comprise sodium acetate or sorbitan monolaurate, sodium lactate, potassium chloride, calcium chloride, triethanolamine oleate, or combinations thereof. In some particular examples, formulation vehicles or carriers include, but are not limited to, glyceryl dioleate, glyceryl monooleate (Arlacel 186/Capmul GMO), lecithin, oleic acid, polyethylene glycol 400, propylene glycol, sorbitan monolaurate (Span 20), sorbitan monooleate (Span 80), sorbitan trioleate (Span 85), poloxamer 407, polysorbate 20, polysorbate 80, and cyclodextrins.

The disclosed compounds are useful as positron emission tomography imaging agents. In imaging formulations, an effective amount of the imaging agent, such as from about 0.01 mCi to about 50 mCi, for example from about 0.1 mCi to about 30 mCi or from 1 to about 15 mCi, including about 1 mCi, about 2 mCi, about 3 mCi, about 4 mCi, about 5 mCi, about 6 mCi, about 7 mCi, about 8 mCi, about 9 mCi, about 10 mCi, about 11 mCi, about 12 mCi, about 13 mCi, about 14 mCi, about 15 mCi, about 16 mCi, about 17 mCi, about 18 mCi, about 19 mCi, about 20 mCi, about 21 mCi, about 22 mCi, about 23 mCi, about 24 mCi, about 25 mCi, about 26 mCi, about 27 mCi, about 28 mCi, about 29 mCi, about 30 mCi may be combined with a pharmaceutically acceptable carrier for use in imaging studies. As used herein, "an effective amount" of the imaging agent refers to an amount sufficient to yield an acceptable image using equipment which is available for clinical use. An effective amount of the imaging agent may be administered in more than one injection. Effective amounts of the imaging agent of the invention will vary according to factors such as the degree of susceptibility of the individual, the age, sex, and weight of the individual, idiosyncratic responses of the individual and dosimetry. Effective amounts of the imaging agent of the invention also will vary according to instrument and film-related factors. The radioactive dose allowed is dependent on the radiation exposure to individual organs. This value is first estimated by calculation from biodistribution data obtained from non-human primates. The radioactive dose administered to a subject should be in the range of 1 to 100 mCi, preferably from about 5 to about 30 mCi or from about 5 to about 15 mCi and typically from about 2 to about 20 mCi, such as about 2 mCi, about 3 mCi, about 4 mCi, about 5 mCi, about 6 mCi, about 7 mCi, about 8 mCi, about 9 mCi, about 10 mCi, about 11 mCi, about 12 mCi, about 13 mCi, about 14 mCi, about 15 mCi, about 16 mCi, about 17 mCi, about 18 mCi, about 19 mCi or about 20 mCi for each application. In the context of PET imaging, disclosed compounds are typically administered as an intravenous (IV) bolus. In some examples, the subject fasts, such as for at least 4 hours, prior to administration of the analogue. The present analogues can be used in the detection and localization of fungi in a subject infected with a fungus, such as an *Aspergillus* species.

The compounds and methods disclosed herein have use in humans and non-human animals.

EXAMPLES

The following examples are intended to be illustrative rather than limiting.

Example 1

Use of Disclosed Isotopically-Labeled Calcofluor Derivatives

This example illustrates the ability of a disclosed isotopically-labeled calcofluor derivative to specifically identify *Aspergillus*-infected tissues.

Figure 2:
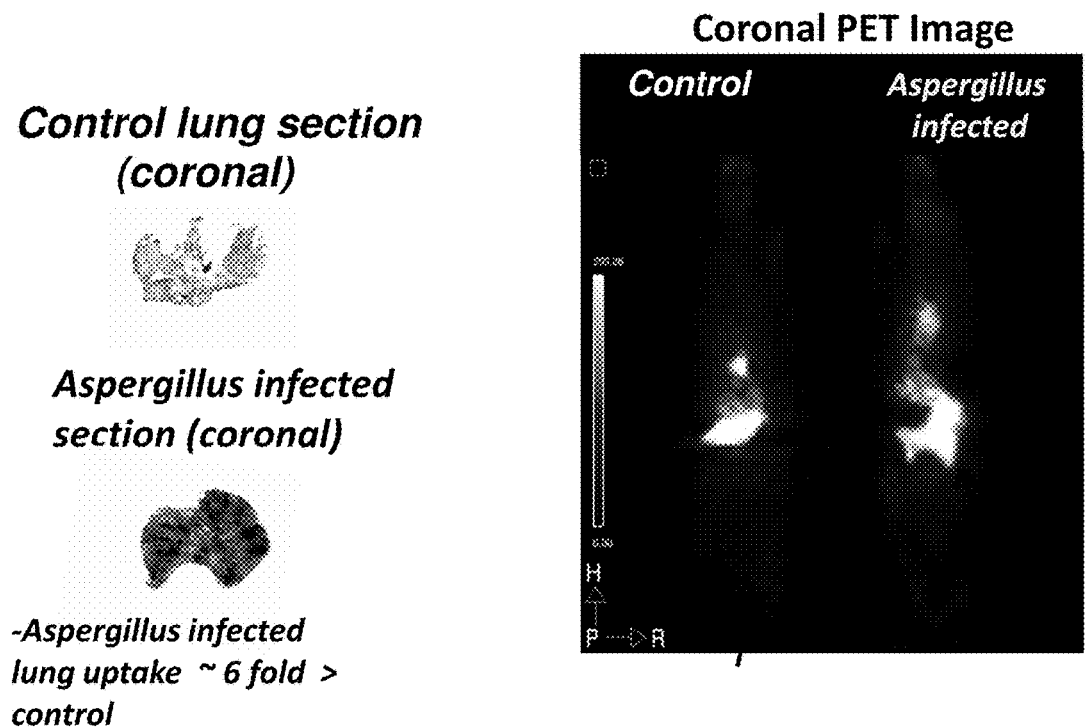
FIG. 2 provides ex vivo autoradiography of the lungs of *Aspergillus*-infected mice compared to controls (left panel) and coronal PET images of *Aspergillus*-infected mice compared to controls (right panel).

Synthetic calcofluor derivatives were synthesized according to synthesis reactions described above which allowed $^{18}F$ labeling of the synthesized compounds enabling the compound to be detected by positron emission tomography (PET) scanning Mono 4-[18f]fluorobenzoate analog from scheme 5 was the particular $^{18}F$-labeled calcofluor derivative used in the present example. This compound was next injected into 20 mice infected with *Aspergillus* and 20 control mice and imaged by PET. These studies determined that lungs of mice infected with *Aspergillus* took up 30% more radioactive tracer than uninfected lungs. FIG. 1 illustrates $^{18}F$-labeled calcofluor derivative uptake in the various tissues in control and *Aspergillus*-infected mice after 2 hours. FIG. 2 provides ex vivo autoradiography of the lungs of *Aspergillus*-infected mice compared to controls (left panel) and coronal PET images of *Aspergillus*-infected mice compared to controls (right panel). It was determined that the *Aspergillus*-infected lung uptake of the disclosed compound was approximately 6 fold greater than the control lung sample. These studies clearly indicate that the disclosed isotopically-labeled calcofluor derivatives are capable of specifically identifying fungi, including *Aspergillus*-infected tissues.

Example 2

Clinical Use of Disclosed Isotopically-Labeled Calcofluor Derivatives

This example describes the clinical use of the disclosed radioactive, isotopically-labeled calcofluor derivatives.

A disclosed radioactive, isotopically-labeled calcofluor derivative is prepared shortly before use, typically within 2 hours of injection, and preferably within less than 1 hour. The presently disclosed synthetic methods for preparing radioactive, isotopically-labeled calcofluor derivatives is particularly facile and thus is uniquely suited to the preparation of $^{18}F$-labeled compounds. The radioactive, isotopically-labeled calcofluor derivative typically has an activity of at least about 0.1 mCi and typically from about 1 mCi to about 300 mCi, preferably from 2 to about 60 mCi, is injected into the subject as an intravenous bolus, typically within less than 5 minutes, and preferably in 1 minute. The intravenous dose achieves target tissue concentrations of 0.04-8.5 µmol/L. In one particular example, a subject is injected with a 1 mCi injection of a disclosed compound with a specific activity of about 1 Ci/micromole, thereby providing 1 nanomol of compound (FW~1000) and about 1 microgram per nanomole. The subject is placed in a PET scanner, and images are obtained at 5 to 10-minute intervals following the injection, up to at least 60 minutes, but not greater than 6 hours, such as between 60 to 120 minutes, when image quality is most satisfactory. Imaging for hours, such as up to or even a day or more (such as up to 48 hours) also may be feasible with $^{64}$Cu-labeled compounds.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound according to the formula

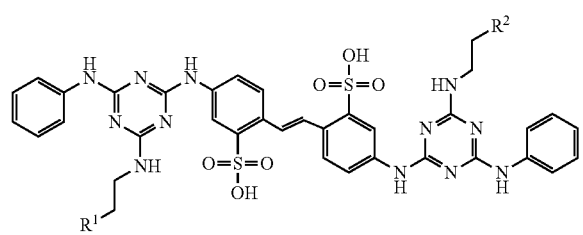

wherein $R^1$ is an amine group, a hydroxyl group, a sulfide group, a carboxylic acid group, an amide group, an alkyl or aryl;
$R^2$ is —NHC(O)—$R^3$-L or —C(O)NH—$R^3$-L, wherein $R^3$ is an aryl or aliphatic; and
L is selected from 1,4,7,10-tetraazacyclododecan-tetraacetic acid (DOTA) and 1,4,7-triazacyclononane-triacetic acid (NOTA).

2. The compound of claim 1, wherein $R^3$ is alkyl.

3. The compound of claim 1, having the formula

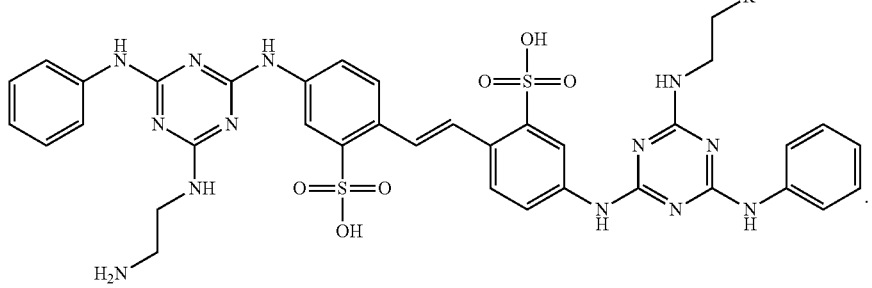

4. A composition comprising the compound of claim 1 and a carrier.

5. A method of detecting a fungal infection in a subject, comprising administering a radiologically-effective amount of the compound of claim 1 chelated to a radiolabel to the subject, and measuring the radioactivity arising from the administration of the compound to the subject.

6. The method of claim 5, wherein measuring the radioactivity comprises using positron emission tomography.

7. The method of claim 5, wherein measuring the radioactivity comprises measuring the radioactivity in the respiratory tract, the gastrointestinal tract, the liver, or the brain of the subject, or a combination of two or more thereof.

8. The method of claim 7, wherein the respiratory tract comprises one or more of nose and nasal passages, paranasal sinuses, pharynx, larynx, trachea, bronchi, and bronchioles, and lungs of the subject.

9. The method of claim 5, wherein the fungal infection is a filamentous fungal infection.

10. The method of claim 9, wherein the filamentous fungal infection is an *Aspergillus* species infection, such as *A. candidus, A. chevalieri, A. clavatus, A. flavipes, A. flavus, A. fumigatus, A. granulosus, A. nidulans, A. niger, A. parasiticus, A. restrictus, A. sydowii, A. tamari, A. ustus, A. versicolor*, and/or *A. wentii* infection.

11. The method of claim 9, wherein the filamentous fungal infection is mucormycosis, *exserohilum*, or phaeohyphomycosis infection.

12. The method of claim 5, wherein the method is used to diagnose a pulmonary lung infection or a condition associated with a pulmonary lung infection.

13. A method of monitoring fungal infection in a subject, the method comprising administering a radiologically effective amount of the compound of claim 1 chelated to a radiolabel to the subject, and measuring the radioactivity arising from the administration of the compound to the subject, thereby monitoring the fungal infection.

14. The method of claim 13, wherein measuring the radioactivity comprises using positron emission tomography.

15. The method of claim 13, wherein measuring the radioactivity comprises measuring the radioactivity in the respiratory tract, the gastrointestinal tract, the liver, or the brain of the subject, or a combination of two or more thereof.

16. The method of claim 13, wherein the respiratory tract comprises one or more of nose and nasal passages, paranasal sinuses, pharynx, larynx, trachea, bronchi, and bronchioles, and lungs of the subject.

17. The method of claim 13, wherein the fungal infection is a filamentous fungal infection.

18. The method of claim 14, wherein the filamentous fungal infection is an *Aspergillus* species infection, such as *A. candidus, A. chevalieri, A. clavatus, A. flavipes, A. flavus, A. fumigatus, A. granulosus, A. nidulans, A. niger, A. parasiticus, A. restrictus, A. sydowii, A. tamari, A. ustus, A. versicolor*, and/or *A. wentii* infection.

19. The method of claim 14, wherein the filamentous fungal infection is mucormycosis, *exserohilum*, or phaeohyphomycosis.

* * * * *